US00PP10876P

United States Patent [19]

Utecht

[11] Patent Number: Plant 10,876

[45] Date of Patent: May 4, 1999

[54] GERANIUM PLANT NAME 'FISFANY'

[75] Inventor: Angelika Utecht, Montabaur, Germany

[73] Assignee: Florfis AG, Switzerland

[21] Appl. No.: 08/969,442

[22] Filed: Nov. 12, 1997

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 9,216 7/1995 Klemm ..... Plt./87.12

P.P. 9,217 7/1995 Trees ..... Plt./87.12

P.P. 9,970 7/1997 Hofmann ..... Plt./87.12

*Primary Examiner*—Howard J. Locker

*Attorney, Agent, or Firm*—Foley & Lardner

[57] ABSTRACT

A new distinct cultivar of Geranium plant name 'Fisfany', particularly characterized by the combined features of bright purple-pink flower color, slightly semi-double, cup-like shaped flowers, medium green foliage with distinct zonation, medium tall and bushy, well-branched plant habit, and early flower response.

1 Drawing Sheet

The present invention comprises a new and distinct cultivar of Geranium, botanically known as *Pelargonium zonale,* and referred to by the cultivar name 'Fisfany'.

'Fisfany' is a product of a planned breeding program which had the objective of creating new geranium cultivars with purple-pink flower color, zoned foliage, and medium tall plant habit.

'Fisfany' was originated from a hybridization made by the inventor Angelika Utecht in a controlled breeding program in Galdar, Gran Canaria, Spain in 1992. The female parent was hybrid seedling No. 2112/3, characterized by pink single flowers and medium green foliage. The male parent of 'Fisfany' was the commercial cultivar 'Penve', (U. S. Plant Pat. No. 9,970), having purple-pink semi-double flowers, light to medium green foliage with slight zonation, very compact habit, and early flowering response.

'Fisfany' was discovered and selected as one flowering plant within the progeny of the stated cross by Angelika Utecht in 1993 in a controlled environment in Galdar, Gran Canaria, Spain.

The first act of asexual reproduction of 'Fisfany' was accomplished when vegatative cuttings were taken from the initial selection in Autumn 1993 in a controlled environment in Galdar, Gran Canaria, Spain, by, or under the supervision of, Angelika Utecht.

Horticultural examination of plants grown from these cuttings initiated in May, 1994 in Hillscheid, Federal Republic of Germany, and continuing therafter, has demonstrated that the combination of characteristics as herein disclosed for 'Fisfany' are firmly fixed and are retained through successive generations of asexual reproduction.

'Fisfany' has not been observed under all possible environmental conditions. The phenotype may vary significantly with variations in environment such as temperature, light intensity and daylength, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic charactrerisics of 'Fisfany', which in combination distinguish this Geranium as a new and distinct cultivar:

1. Intense purple-pink flower color and a distinct white eye.

2. Slightly semi-double, open, cup-like shaped flowers.
3. Medium green foliage with distinct zonation.
4. Medium tall, well branched plant habit.
5. Early spring flowering response.

Of the many commercial cultivars known to the present inventor, the most similar in comparison to 'Fisfany' is the paternal parent 'Penve'. Reference is made to attached Chart A which compares certain characteristics of 'Fisfany' to those same characteristics of 'Penve'. In general comparison to 'Penve', 'Fisfany' has somewhat larger flowres with fewer inner petals and a more distinct white zone at the base of the upper petals. The color and shape of flowers in general are similar for both cultivars. 'Fisfany' grows more vigorously, and leaf zonation is somewhat more distinct.

The accompanying photographic drawing shows typical flower and foliage characteristics of 'Fisfany', with colors being as true as possible with illustrations of this type.

In the following description, color references are made to The Royal Horticultural Society Colour Chart. The color values were determined indoors in from flowers taken from plants grown in a greenhouse in May 1995 in Hillscheid, Germany.

Classification:

*Botanical.*—A hybrid of the species *Pelargonium zonale* l'Hert.

*Commercial.*—Zonal geranium, cv. 'Fisfany'.

Inflorescence

Umbel:

*Shape.*—Semi-spherical.

*Average diameter.*—110 mm.

*Average depth.*—66 mm.

*Peduncle length.*—175 mm.

*Pedicel length.*—21 mm.

*Pedicel color.*—Medium green to light red.

*Number of flowers per umbel.*—About 30–50.

Corolla:

*Average diameter.*—47 mm. *Form.*—Semi-double.

*Number of petals.*—6–8.

*Number of petaloids.*—0–2. *Color* (*general tonality from a distance o three meters.*).—Purple to purple-pink.

*Color of upper petals.*—Between 66 B and 74 B.

*Markings, of upper petals.*—Distinct white zone at the base.

*Color of lower petals.*—Between 66 B and 74 B.

*Color of lower surface of petals.*—67 B.

*Color of sepals.*—Light green, occasionally a fleck of anthocyanin.

*Number of sepal.*—5.

Bud:

*Shape.*—Elliptic.

*Color* (*adaxial*).—Light to medium green, occasionally light red at the base.

*Color* (*abaxial*).—Purple-pink.

Reproductive organs:

*Androecium.*—7–9 fertile anthers; yellow-orange pollen.

*Gynoecium.*—5–6 -lobed stigma, purple with red filament.

*Seed set.*—May develop a few seeds in late Summer and Autumn.

Spring flowering response period: In Hillscheid, Germany, in 1995 plants had on average 1.4 flowers opened 11 weeks after planting of unrooted cuttings.

Outdoor flower production: The flower count in 1994 in Hillscheid, Germany indicated about 25 umbels per plant for May through August observation period.

Durability: Good shatter resistance, good rain resistance.

Plant

Foliage:

*Form.*—Kidney-shaped.

*Margin.*—Bicrenated.

*Size of leaf.*—100 mm.

*Color of upper surface.*—Medium green, approximately 137 C.

*Color of zonation.*—Brown, about 166 A.

*Tolerance of botrytis.*—Average.

General appearance and form:

*Internode length.*—15 mm.

*Branching pattern.*—5.9 branches.

*Height of plants.*—30 cm (in September, based on 35-week old plants).

CHART A

| | FISFANY | PENVE |
|---|---|---|
| Diameter of flower | 47 mm | 43 mm |
| No. of petals | 6–8 | 7–9 |
| Zonation on foliage | medium | weak |
| Peduncles | 17.5 cm | 13.5 cm |
| Height of plants | 30 cm | 25 cm |

I claim:

1. A new and distinct cultivar of Geranium plant named 'Fisfany', as illustrated and describe.

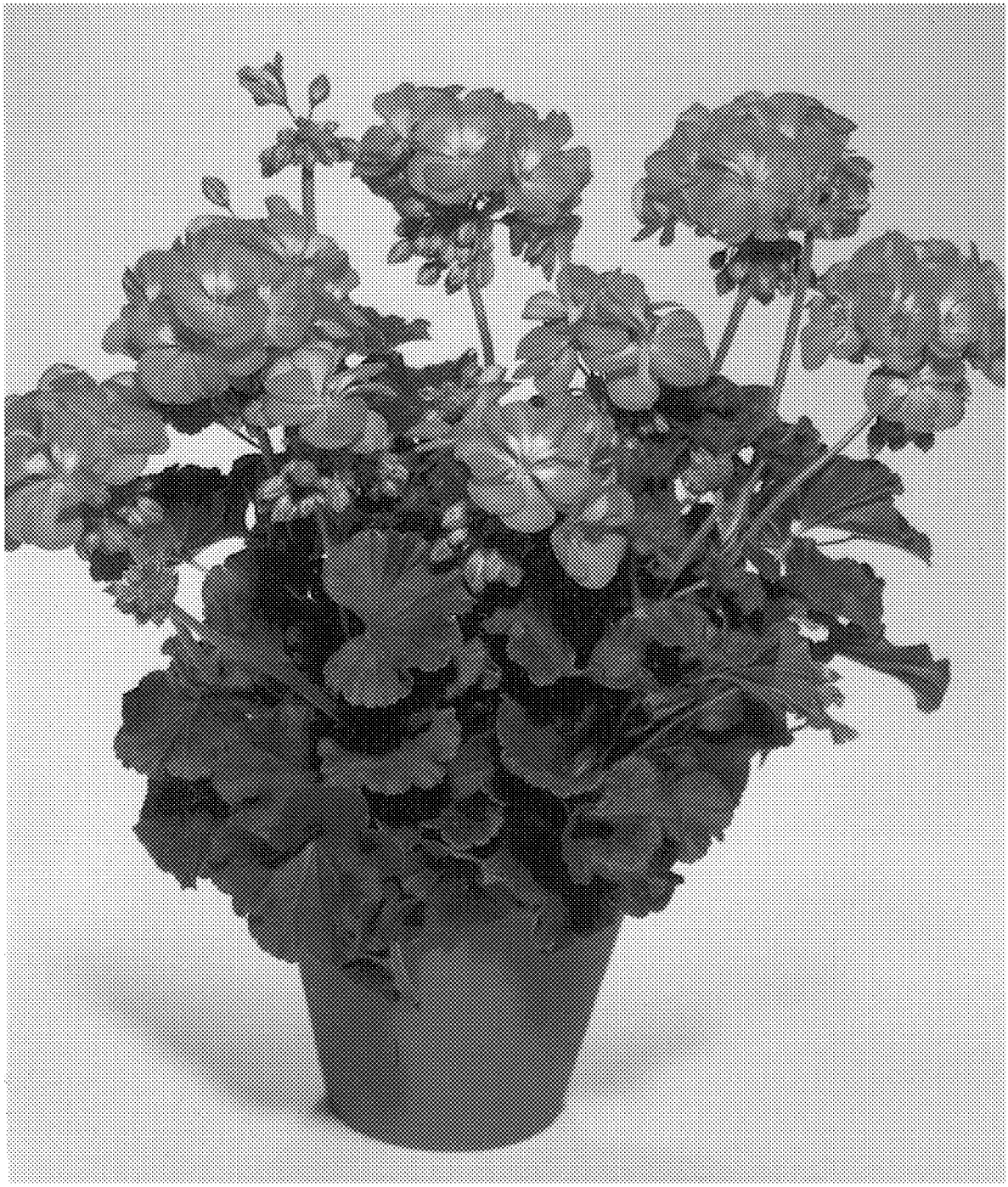

* * * * *